United States Patent [19]

Bischoff et al.

[11] Patent Number: 4,670,260

[45] Date of Patent: Jun. 2, 1987

[54] ANTIBIOTIC FOR ANIMAL FEEDS

[75] Inventors: Erwin Bischoff, Wuppertal; Hartwig Müller, Velbert; Olga Salcher, Wuppertal; Friedrich Berschauer, Wuppertal; Martin Scheer, Wuppertal; Anno de Jong, Wuppertal; Klaus Frobel, Wuppertal, all of Fed. Rep. of Germany

[73] Assignee: Bayer Aktiengesellschaft, Leverkusen, Fed. Rep. of Germany

[21] Appl. No.: 802,776

[22] Filed: Nov. 27, 1985

[30] Foreign Application Priority Data

Nov. 30, 1984 [DE] Fed. Rep. of Germany ....... 3443681

[51] Int. Cl.$^4$ .......................... A61K 35/74; C12P 1/06
[52] U.S. Cl. .................................... 424/121; 424/122; 435/169
[58] Field of Search ................. 424/121, 122; 435/169

Primary Examiner—Jerome D. Goldberg
Attorney, Agent, or Firm—Sprung, Horn, Kramer & Woods

[57] ABSTRACT

A novel antibiotic for combating bacteria and promoting animal growth is obtained by cultivating Streptomyces strain BA 9.

7 Claims, 3 Drawing Figures

ANTIBIOTIC FOR ANIMAL FEEDS

The present invention relates to a new organic chemical compound, to microbiological processes for its preparation, and to its use as an antibiotic and as an agent for promoting the growth, and for increasing the utilization of feed of livestock.

The compound according to the invention can be characterized by the following properties and parameters:

1. IR KBr absorption spectrum of the sodium-containing antibiotic according to FIG. 1 (abscissa: wave number in cm$^{-1}$, ordinate absorption).

Figure 1:
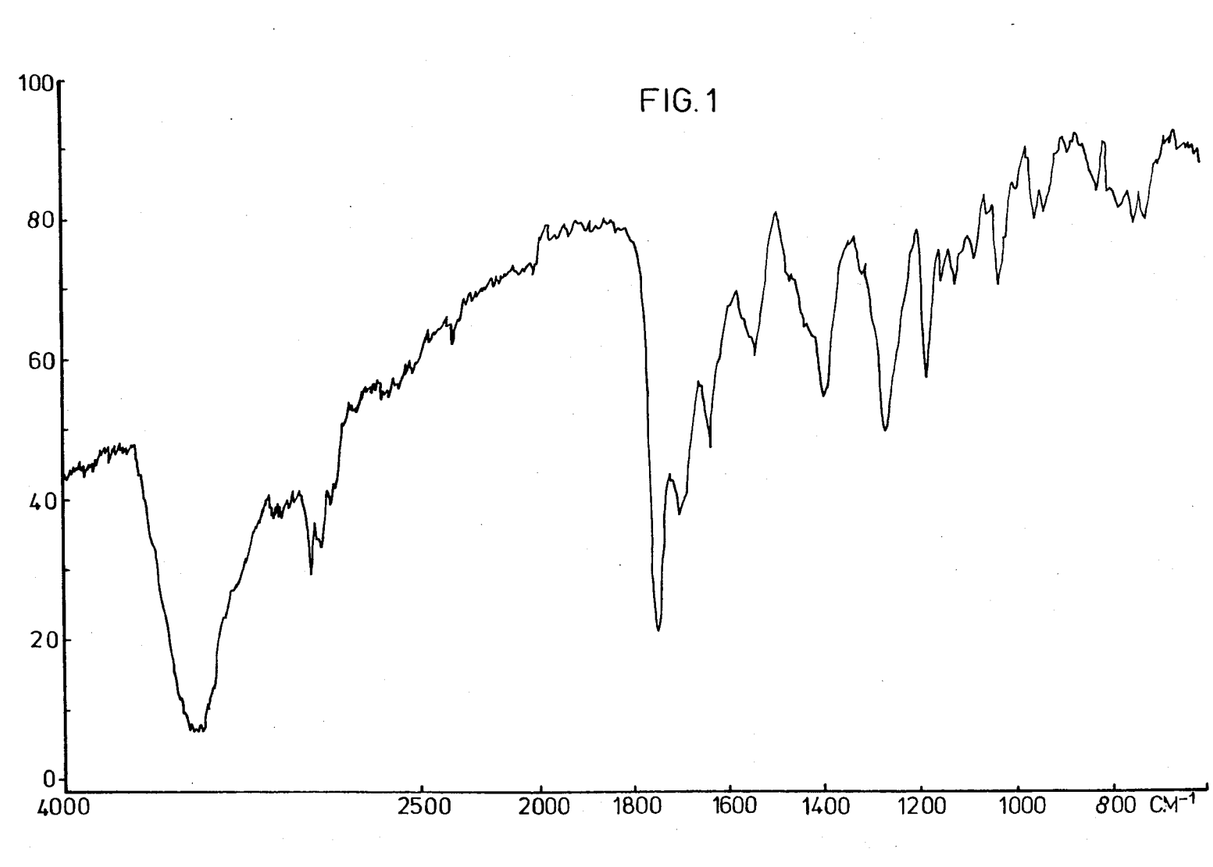

It shows characteristic absorption bands at the following wavelengths (expressed in cm$^{-1}$):

| | |
|---|---|
| 3456 | 1265 |
| 2960 | 1178 |
| 2910 | 1145 |
| 1750 | 1115 |
| 1700 | 1030 |
| 1635 | 950 |
| 1540 | 930 |
| 1395 | 825 |

2. $^1$H nuclear magnetic resonance spectrum, according to FIG. 2, reported in parts per million and vibrations per second.

Figure 2:
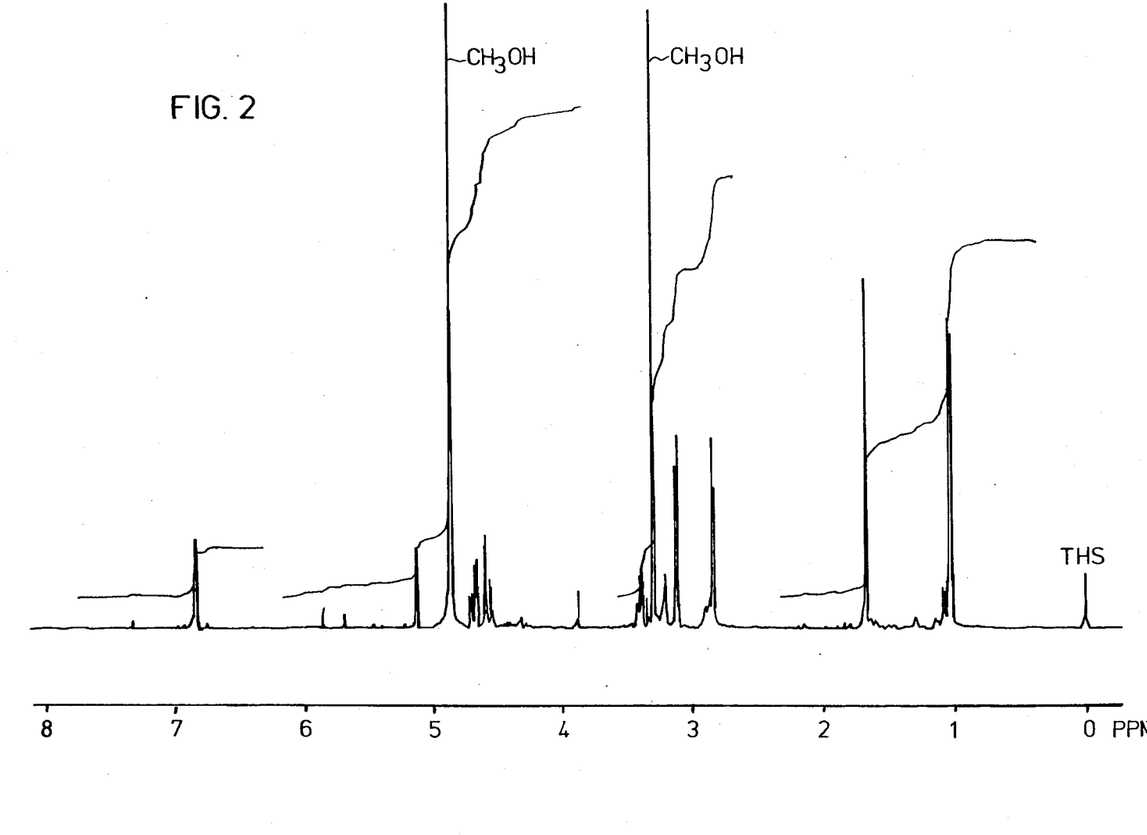

It was recorded at a field strength of 300 MHz on a solution of the antibiotic in deuterated methanol using tetramethylsilane in deuterated methanol as the internal standard.

Figure 3:
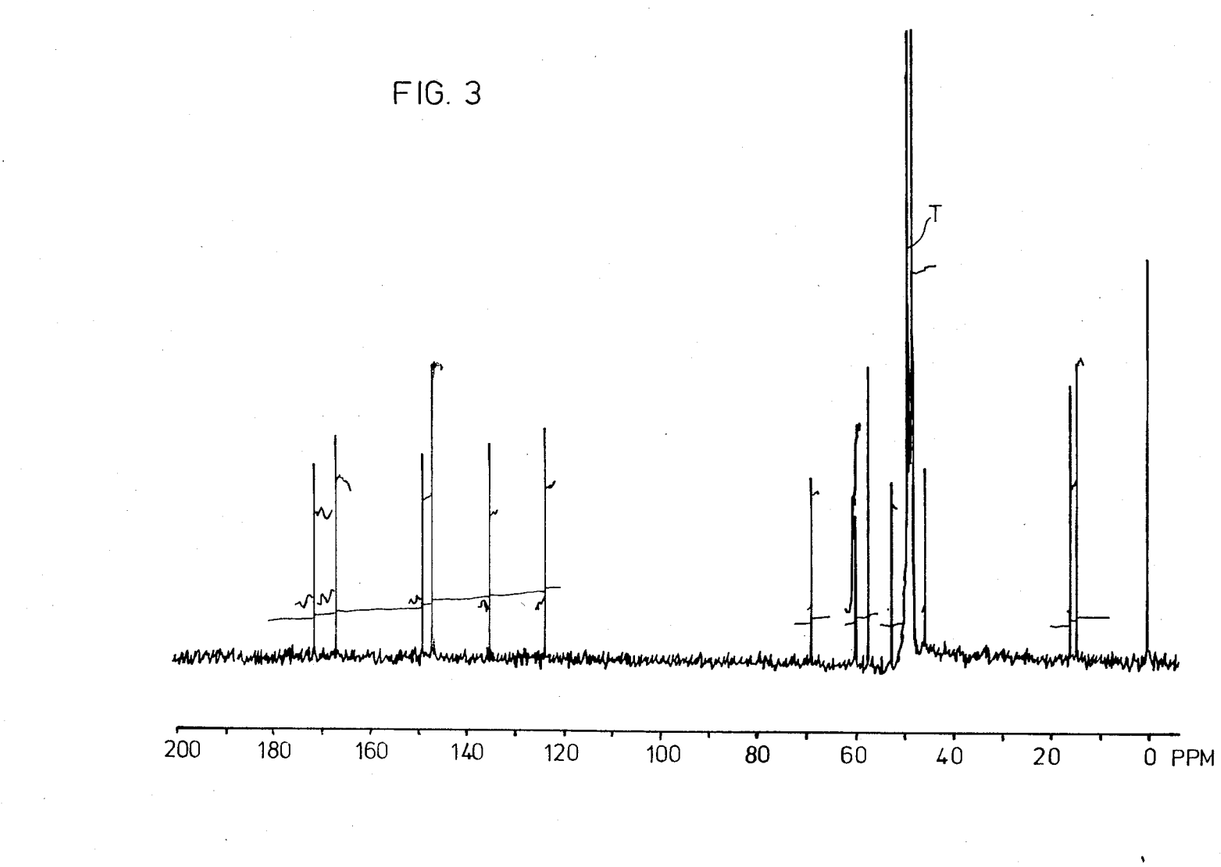

3. The 13C nuclear magnetic resonance spectrum according to FIG. 3. It was recorded in the same solution as the $^1$H spectrum at a field strength of 75.48 MHz.

4. Elemental analysis (after drying under high vacuum at 30° C. for 2 days): C 61.1–62.3%; H 5.2–6.4%; O 27.5–30.0%.

5. Empirical formula: $(C_{14-16}H_{16-20}O_{4-6})_n$.

It needs to be pointed out here that the error in the elemental analysis of high molecular weight natural substances can be larger than is generally customary; for this reason, accurate determination of the empirical formula is not possible (R. B. Woodward, Angew. Chem. 69, 50–51 (1957)).

6. Empirical formula of the Na-containing compound: $(C_{29-31}; H_{33-37}; O_{9-11}; Na)_n$.

7. The compound is readily soluble in ethyl acetate, chloroform, MeOH and lower alcohols; sparingly soluble in water.

8. After chromatography on thin-layer silica gel plates, the compound can be stained with FeCl$_3$/H$_2$SO$_4$. The reagent was prepared by the customary procedures (see E. Stahl, Dünnschichtchromatographie (Thin-Layer Chromatography), 2nd edition, published by Springer, Berlin, Heidelberg, New York 1967).

9. The antibacterial action of the compound is shown in Table 1.

Furthermore, the present invention relates to new microorganisms of the family Streptomycetaceae, which, on cultivation in a nutrient medium containing sources of carbon and nitrogen together with mineral salts, produce a compound which has the properties and parameters listed above under (1) to (9), the IR KBr absorption spectrum shown in FIG. 1 being of particular importance.

Of these, the new microorganism strain BA 9 of the genus Streptomyces is particularly important within the scope of the present invention.

The enrichment and isolation of the strain was carried out by the customary methods of isolation of Actinomycetes, by plating out suspensions of soil samples on Petri dishes, incubating for four to six weeks, and repeated subculturing of individual colonies (Williams, S. T. and Cross, T. (1971). Actinomycetes. In Methods in Microbiology 4, 295-334. Booth, C. (editor), London-New York: Academic Press).

The new Streptomyces strain with the laboratory identification BA 9 was deposited at the Deutsche Sammlung von Mikroorganismen (German Collection of Microorganisms), Griesebachstrasse 8, 3400 Göttingen, FRG, under the number DSM 3025 on Aug. 6th, 1984.

It has also been found that the compound according to the invention is obtained when suitable microorganisms of the family Streptomycetaceae are cultivated under aerobic conditions in a nutrient medium which contains sources of assimilable carbon and nitrogen together with mineral salts, and the compound is isolated by customary methods.

The Streptomycetes strain BA 9 (and its mutants and variants), in particular, can be used to carry out the process according to the invention.

This strain belongs to the bacteria of the order Actinomycetales, the family Streptomycetaceae and the genus Streptomyces. It was isolated from soil.

The taxonomic identification of the strain BA 9 was carried out in accordance with *Bergey's Manual of Determinative Bacteriology* 8th ed. (1974) and the *International Journal of Systematic Bacteriology* 16, 313–340 (1966) and *The Prokaryotes* 2, 2028–2090 (1981).

1. Morphology

Good sporulation was observed only on inorganic salts starch agar (ISP medium No. 4, for composition, see page 4). On other media (ISP media Nos. 1+-3 and 5), a little aerial mycelium or only substrate mycelium was formed. + ISP medium No. 1, supplemented with 10 g/l D-mannitol (for composition, see page 5).

Aerial mycelium (ISP medium No. 4; 28° C.; 7 d):
Color: gray after 7 d
Spore chains: spira type
Spores: slightly rough (electron microscopy), cylindrical, about 1.1–1 μm wide, 1.4–1.6 μm long.

Substrate mycelium:
Color: red-brown, especially on ISP medium Nos. 3 and 5

Cell-wall analysis:
Cell wall type I, the main constituents are LL-diaminopimelic acid and glycine.

2. Physiology

The optimum temperature is 28° (ISP medium No. 1+, 5 d). No growth was observed on ISP medium No. 7 (tyrosine agar). Melanin is formed on ISP medium No. 6. The growth is inhibited by chloramphenicol (10 μg); erythromycin (10 μg), sulphafurazole (100 μg), streptomycin (10 μg), tetracycline (10 μg), chephaloridine (5 μg) fusidic acid (10 μg), lincomycin (10 μg) and novobiocib (5 μg) (ISP medium No. 1+, 28° C., 2 d). Growth was good (substrate mycelium) on ISP media Nos. 3, 4 and 5, with sparse formation of aerial mycelium on ISP medium Nos. 3 and 5.

ISP medium No. 4 (inorganic salts-starch agar):

| | |
|---|---|
| Starch (soluble) | 10.0 g |
| $K_2HPO_4$(anhydr.) | 1.0 g |
| $MgSO_4 7H_2O$ | 1.0 g |
| NaCl | 1.0 g |
| $(NH_4)_2SO_4$ | 2.0 g |
| $CaCO_3$ | 2.0 g |
| Trace element solution | 1.0 mL |
| $H_2O$ deionized | 1,000.0 mL |
| pH 7.0–7.4 | |
| Trace element solution | |
| $FeSO_4 7H_2O$ | 0.1 g |
| $MnCl_2 4H_2O$ | 0.1 g |
| $ZnSO_4 7H_2O$ | 0.1 g |
| $H_2O$ deion. | 100.0 ml |

ISP media No. 1 (tryptone-yeast extract-agar) supplemented with mannitol:

| | |
|---|---|
| Bacto tryptone (difco) | 5.0 g |
| Bacto yeast extract (difco) | 3.0 g |
| Bacto agar (difco) | 15.0 g |
| D-mannitol | 10.0 g |
| $H_2O$ deion. | 1,000.0 mL |

For other media, see Int. J. Syst. Bact. 16, 313–340 (1966).

Test for the utilization of carbon (C) sources:

The utilization of C sources was checked on basal ager in accordance with Int. J. Syst. Bact. 16, 313–340 (1966). For the negative control, the growth on basal ager without a C source was compared.

| C source (10 g/l) | Growth* |
|---|---|
| Control (no C source) | − |
| D-glucose | + |
| D-xylose | − |
| L-arabinose | − |
| L-rhamnose | + |
| D-fructose | + |
| D-galactose | + |
| raffinose | − |
| D-mannitol | + |
| meso-inositol | − |
| salicin | − |
| sucrose | − |
| ribose | − |
| mannose | − |
| maltose | − |
| lactose | + |
| mellibiose | − |
| cellulose | − |
| acetate | − |

*+ = growth
− = no growth

The strain BA 9, which was isolated from a soil sample from Israel (Jerusalem), may be assigned on the basis of the morphological data to the gray series of Streptomycetes (Cinereus group). The physiological properties do not agree completely with any of the strains described in Bergey's manual.

Taxonomic designation: Streptomyces sp.

The nutrient media used for the process for the preparation of the compound according to the invention contain the customary sources of carbon and nitrogen and the necessary salts. The following may be used as sources of carbon:

Carbohydrates, in particular polysaccharides, such as, for example, starch, and monosaccharides, such as, for example, glucose or fructose. Furthermore, sugar alcohols, such as, for example, mannitol or glycerol, can also be used, as well as naturally occurring mixtures, such as, for example, malt extract or distillers' solubles, and mixtures of the options mentioned.

The customary sources of nitrogen can be used as the source of nitrogen, for example proteins, protein hydrolyzates, amino acids, ammonium salts, naturally occurring complex materials such as soy bean flour, meat extracts, yeast extracts, powdered milk and suitable mixtures of these.

Mineral salts are necessary as auxiliaries in the nutrient medium, for example phosphates, sulphates or chlorides, of potassium, of sodium, of calcium, of magnesium, iron, zinc and manganese. The concentration of these substances can vary within wide limits, some of the necessary concentrations of the mineral salts are contained as impurities in the abovementioned sources of carbon or nitrogen or in the water used.

Furthermore, it is possible to use as auxiliaries antifoam agents of a very wide variety of types, such as, for example, polyols or silicones.

The process for the preparation of the compound according to the invention can be carried out using the customary solid, semisolid or liquid nutrient media. Aqueous liquid nutrient media are preferred.

The inoculation of these nutrient media is carried out by generally customary methods, for example via slant tubes or flask cultures.

The culture is carried out under aerobic conditions and can be carried out by the generally customary methods, such as by use of shake cultures, for example in shaken flasks, of air-agitated cultures or of submerged cultures. The cultivation is preferably carried out in the aerobic submerged method in aeroated fermenters, for example in customary tanks for submerged fermentation. It is possible to carry out the culture continuously or discontinuously. It is preferably carried out discontinuously.

The process for the preparation is carried out under aerobic conditions; the culture can be carried out by customary methods, for example using shake cultures or aerated fermenter cultures. The percentage ratios of the constituents of the nutrient solution can vary within wide limits, in general 0.5–8%, preferably 0.6–6%, being sources of carbon, 0.1–5%, preferably 0.5–2%, being sources of nitrogen, and the salts being present in customary concentrations, preferably in the range between 0.001 and 0.5% by weight. The antifoam agents are present in a concentration of 0.5% strength. The temperatures employed for sterilization are 100°–140° C., preferably 120°–130° C.

The pH of the growing cultures should preferably be maintained between about 6 and about 8.5, in particular between 6.5 and 8.0. Too great a decrease of the pH into the acid range can be prevented by addition of an organic or inorganic base, preferably $CaCO_3$. As is customary in the technology of fermentation, it is also possible for automatic control of pH to be carried out, in which sterile organic or inorganic acid, for example $H_2SO_4$, or sterile alkali, for example NaOH, is injected into the culture solution at intervals.

It is advantageous to ensure that the microorganisms are brought into adequate contact with oxygen and the nutrients. This can be brought about by the generally customary methods, such as shaking and stirring.

The cultivation temperature can be between about 16° and about 42° C., preferably between 24° and 32° C., and it is particularly preferably about 28° C. The cultivation time can be varied widely, the composition of the nutrient medium and the cultivation temperature, for example, being of importance. The optimum conditions in each instance can readily be determined by all those skilled in the area of microbiology.

It has emerged that the amount of the compound according to the invention which is accumulating in the culture broth generally reaches its maximum about 1 to 7, preferably 1 to 4, days after the start of cultivation.

As is general with microbiological processes, foreign infections of the culture medium should be prevented. The customary measures are applied for this purposes, such as sterilization of the nutrient media, of the culture vessels and of the air necessary for the aeration. It is possible to use, for example, steam or dry sterilization to sterilize the equipment.

If undesired amounts of foam are produced during the cultivation, it is possible to add customary chemical foam suppressants, for example liquid fats and oils, oil/water emulsions, paraffins, higher alcohols, such as octodecanol, silicone oils, and polyoxyethylene or polyoxypropylene compounds. Foam can also be suppressed or eliminated by means of the customary mechanical equipment (which makes use of, for example, centrifugal forces).

The compound according to the invention can be isolated from the culture medium by generally customary physico-chemical methods. The isolation can be carried out by, for example, the customary extraction processes, precipitation processes and/or chromatographic processes. The isolated compound can also undergo final purification using the methods mentioned. However, final purification is unnecessary in many cases since the impurities which are, where appropriate, present do not have an adverse effect on the activity of the compound.

In order to find, in the abovementioned isolation and purification methods, the fractions in which the compound according to the invention is present in the highest concentration or purity, it is preferable to use determination of the antibiotic activity. Particularly suitable test organisms for this purpose are *Staphylococcus aureus* 1756, Bac. subtilis ATCC 6633 and *Escherichia Coli* 14.

The isolation and purification of the compound according to the invention can be carried out, for example in the case where a liquid aqueous nutrient medium is used, as follows: after its accumulation in the culture supernatant, the culture filtrate and mycelium are separated by customary methods (for example centrifugation).

The compound according to the invention can be isolated and, where appropriate, purified from the culture filtrate using customary extraction processes, precipitation processes and/or chromatographic processes. The chromatography can be carried out in the form of column chromatography. It is possible to use the customary inorganic or organic adsorbents as the adsorbent, such as, for example, alumina, silica gel, magnesium silicate, active charcoal, cellulose, cellulose derivatives, synthetic resins, such as polyamides, for example acetylated polyamide, or dextran gels. A very wide variety of solvents or solvent mixtures in which the compound according to the invention is soluble can be used as the mobile phase. It is preferable to use methanol or a mixture of chloroform and methanol (for example 1:1 parts by volume).

Chromatographic processes are preferably used for the isolation of the compound according to the invention, for example non-specific adsorption onto hydrophobic sorbents or, on the other hand, gel diffusion chromatography. These are the methods known for the purification of natural substances which are sparingly soluble in water.

For commercial preparation, the compound according to the invention is preferably obtained by adsorption and subsequent desorption on a hydrophobic carrier resin (for example Lewapol; a hydrophobic carrier resin of BAYER AG). The desorption can be carried out with, for example, short-chain aliphatic alcohols, preferably methanol or ethanol.

A fraction pre-purified in this way can, in turn, be purified by the customary methods. It is possible and preferable to use gel diffusion chromatography for this. Chromatography on Sephadex LH-20 ® is successful. A product obtained in this manner is generally more than 50% pure.

The process used for the isolation and purification of the compound according to the invention is preferably as follows:

The mycelium is removed from the culture broth, preferably by centrifugation, and is extracted several times, preferably twice, with a solvent which is miscible with water. The solvents which can be used are lower alkyl alcohols ($C_1$–$C_4$), such as ethanol or isopropanol, and ketones, acetone being particularly preferred. The aqueous/organic solution is concentrated in vacuo to, for example, about 1/20 of the volume of the culture broth, and is freeze-dried.

This crude product is suspended in water, and the compound according to the invention is extracted using a solvent which is immiscible with water, such as, for example, esters of acetic acid or ketones. The compound can be isolated from this extract by customary chromatographic methods, preferably chromatography on Sephadex LH 20 ® and on silica gel.

The compound can also be isolated from the culture filtrate by adsorption onto active charcoal or onto suitable resins. A particularly suitable method has proved to be binding of the compound according to the invention onto non-specific adsorber resins based on polystyrene (for example Amberlite XAD supplied by Roehm & Haas, or Lewatit OC 1031 supplied by Bayer). The compound according to the invention is desorbed into fractions using mixtures of water and organic solvents, in particular water/methanol. The active fractions found by testing against *Staphylococcus aureus* 1756 are concentrated under reduced pressure until the organic solvent has been completely removed, and the residue is suspended in about 1/100 of the volume of the culture filtrate and is freeze-dried.

The lyophilizate is now suspended in water and extracted with, preferably, ethyl acetate or other solvents which are immiscible with water. The compound according to the invention can be obtained from the extract by customary chromatographic methods, preferably chromatography on Sephadex LH 20 ® and silica gel.

As already mentioned, the compound according to the invention has antibacterial activity. This may be shown as follows:

Overnight cultures of various test organisms are prepared: sterilized, pre-temperatured medium is inoculated with 1 ml portions of these batches. The test organisms are then incubated at a suitable temperature on a rotating shaking machine until the cells have reached the log phase. They are then diluted with sterile, preequilibrated nutrient medium to an $OD_{578}$ (OD=optical density=apparent extinction) of 0.02–0.04. The active compound is added to these suspensions, and various concentrations of active compound are set up by means of serial dilutions. When the control batches (containing no active compound) show pronounced turbidity after suitable incubation, the MIC (MIC=minimum inhibitory concentration) is determined, and this corresponds to the lowest concentration of active compound in which the batches show no turbidity.

The experiments were carried out with antibiotic medium 3. The incubation time up to measurement, the initial OD and the incubation temperature of the various test organisms may be seen in Table 1 which follows:

TABLE 1

| Test organism | MIC μg/ml | Incubation temperature °C. | Incubation time up to measurement | $OD_{578}$ |
|---|---|---|---|---|
| Bacillus brevis | 2.5 | 37 | 6 h | 0.02 |
| Bacillus cereus | 0.6 | 37 | 5 h | 0.04 |
| Bacillus subtilis ATCC 6633 | 0.6 | 37 | 4.5 h | 0.02 |
| Ecoli 14 | 1.3 | 37 | 4 h | 0.02 |
| Ecoli A 261 | 2.5 | 37 | 4 h | 0.02 |
| Proteus vulgaris | 1.3 | 37 | 4 h | 0.04 |
| Pseudomonas aeruginosa | 10 | 27 | 4 h | 0.02 |
| Pseudomonas aeruginosa Ellsworth | 10 | 37 | 4 h | 0.03 |
| Serratia mareescens | 2.5 | 30 | 4.5 h | 0.02 |
| Staphylococcus aureus A 1756 | 1.3 | 37 | 4 h | 0.02 |
| Staphylococcus aureus P 209 | 0.6 | 37 | 4 h | 0.02 |

The compound according to the invention exhibits a good antibacterial action against various Gram-positive and Gram-negative organisms:

It can be used as a therapeutic agent in both human and veterinary medicine. Particular mention should be made of its suitability for preventing and healing of dysentery of pigs and ketosis of cattle.

The compound according to the invention can be used in preparations having antibacterial activity. Particularly preferred preparatins having antibacterial activity are those which contain the compound according to the invention or its alkali metal or alkaline earth metal salts.

The pharmaceutical preparations according to the invention contain, in addition to the new compounds according to the invention, in the customary manner nontoxic, inert, pharmaceutically suitable excipients. Examples of pharmaceutically suitable excipients of this type are fillers and extenders, binders, humectants, solution retarders, absorption accelerators, wetting agents, adsorbents or lubricants, which may have a solid, semisolid or liquid consistency. Pharmaceutically suitable excipients of this type are known to those skilled in the art.

Preferred pharmaceutical preparations which may be mentioned are tablets, coated tablets, capsules, pills, granules, suppositories, solutions, suspensions and emulsions, pastes, ointments, gels, creams, lotions, powders and sprays. The manufacture of these preparations is carried out by known methods in the customary manner, for example by mixing the new compound according to the invention with the customary excipients and additives. The active compound should be present in the pharmaceutical preparations mentioned in a concentration of about 0.1 to 99.5, preferably about 0.5 to 95, % by weight of the total mixture.

The compound according to the invention can be used in all areas of livestock breeding as an agent for the promotion and acceleration of growth and for the improvement of the utilization of feed of healthy and diseased livestock.

In this contrast, the efficacy of the active compound is substantially independent of the species and sex of the livestock. The active compounds prove to be especially valuable for the rearing and management of young and fattening livestock.

Examples of livestock for which the active compound can be used for the promotion and acceleration of growth, for improving the utilization of feed and for improving the meat/fat ratio in the carcass and which may be mentioned are the following useful and ornamental livestock:

Warm-blooded species such as cattle, pigs, horses, sheep, goats, cats, dogs, rabbits, fur-bearing livestock, for example mink and chinchilla, poultry, for example chickens, geese, ducks, turkeys, pigeons, parrots and canaries, and cold-blooded species, such as fish, for example carp, and reptiles, for example snakes.

The amount of the active compound which is administered to the livestock to achieve the desired effect can be substantially varied because of the favorable properties of the active compound. It is preferably about 0.005 to 50, in particular 0.1 to 10, mg/kg of body weight per day. The duration of administration can be from a few hours or days up to several years. The appropriate amount of the active compound and the appropriate duration of administration depend, in particular, on the species, the age, the sex, the state of health and the type of management and feeding of the livestock, and can readily be determined by all those skilled in the art.

The active compound is administered to the livestock by customary methods. The type of administration depends, in particular, on the species, the behavior and the state of health of the livestock. Thus, the administration can be carried out orally or parenterally once or several times a day at regular or irregular intervals.

For reasons of convenience, in most cases oral administration is to be preferred, in particular in the rhythm of the intake of food and/or drink by the livestock.

The active compound can be administered as a pure substance mixture or in a formulated form, that is to say mixed with non-toxic inert excipients of any desired type, for example with excipients and in formulations as are customary in nutritional preparations.

The active compound is, where appropriate, administered in the formulated form together with pharmaceutically active compounds, mineral salts, trade elements, vitamins, proteins, fats, colorants and/or flavorings in a suitable form.

Oral administration together with the feed and/or drinking water is to be recommended, depending on the requirement the active compound being added to the total amount or to only portions of the feed and/or drinking water.

The active compound is added to the feed and/or drinking water by customary methods, by simply mixing as a pure substance mixture, preferably in the finely divided form, or in a formulated form mixed with edible, nontoxic excipients, where appropriate in the form of a premix or a feed concentrate.

The feed and/or drinking watwer can contain, for example, the active compound in a concentration by weight of about 0.005 to 50, in particular 0.1 to 10, ppm. The optimum level of the concentration of the active compound in the feed and/or drinking water depends, in particular, on the amount of feed and/or drinking water taken in by the livestock and can readily be determined by all those skilled in the art.

The type of the feed and its composition has no relevance in this context. All conventional or special feed compositions can be used, and these preferably contain the customary balance of energy carriers and builders which are necessary for a balanced diet, including vitamins and minerals. For example, the feed can be composed of vegetable materials, for example, hay, roots, cereals, cereals by-products, animal materials, for example meat, fats, bone meal, fish products, vitamins, for example vitamin A, D complex and B complex, proteins, amino acids, for example DL-methionine and inorganic substances, for example lime and sodium chloride.

Feed concentrates contain the active compound in addition to edible substances, for example rye meal, corn meal, soy bean meal or lime, where appropriate with other nutrients and builders, and proteins, mineral salts and vitamins. They can be produced by the customary mixing methods.

It is possible, preferably in premixes and feed concentrates, for the active compound, where appropriate, to be protected from air, light and/or moisture by suitable agents covering its surface, for example with nontoxic waxes or gelatine.

An example of the composition of a chicken rearing feed which contains the active compound:

200 g of wheat, 340 g of corn, 361 g of coarse soy bean meal, 60 g of beef suet, 15 g of dicalcium phosphate, 10 g of calcium carbonate, 4 g of iodized sodium chloride, 7.5 g of vitamin/mineral mixture and 2.5 g of active compound premix result, after careful mixing, in 1 kg of feed.

1 kg of feed mixture contains the following: 600 I.U. of vitamin A, 100 I.U. of vitamin D, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of Mn $SO_4 \times H_2O$, 140 mg of Zn $SO_4 \times 7\ H_2O$, 100 mg of Fe $SO_4 \times 7\ H_2O$ and 20 mg of Cu $SO_4 \times 5\ H_2O$.

The active compound premix contains the active compound in the desired amount, for example 10 mg, as well as 1 g of DL-methionine and sufficient soy bean meal to produce 2.5 g of premix.

An example of the composition of a pig rearing feed which contains the active compound according to the invention:

630 g of coarse feed cereal meal (composed of 200 g of corn, 150 g of coarse barley meal, 150 g of coarse oatmeal and 130 g of coarse wheat meal), 80 g of fish meal, 60 g of coarse soy bean meal, 60 g of cassava meal, 38 g of brewer's yeast, 50 g of vitamin/mineral mixture for pigs (composition, for example, as for chicken feed), 30 g of linseed cake meal, 30 g of corn gluten meal, 10 g of soy bean oil, 10 g of sugarcane molasses and 2 g of active compound premix (composition, for example, as for chicken feed) result, after careful mixing, in 1 kg of feed.

The feed mixtures indicated are adjusted to be appropriate preferably for the rearing and fattening of chickens and pigs, but they can also be used in the same or similar composition for the rearing and fattening of other livestock.

As already mentioned, it is not absolutely necessary to use the purified and isolated active compound. It is also possible to use the culture broth resulting during its preparation, without purification, where appropriate after drying. For many purposes, it is also adequate to use crude forms of the active compounds according to the invention, without previous final purification.

The preparation of the new compound according to the invention can be illustrated by the examples which follow:

EXAMPLE 1

The nutrient solution in which the production strain Streptomyces sp. BA 9 is cultivated is composed of defatted soy bean meal, 3% glycerol (87% pure) 3%, $CaCO_3$ 0.2% in tapwater. The nutrient solution is sterilized at 121° C. for 40 min. A 1,000 ml conical flask which contains 150 ml of this nutrient solution is inoculated with the production strain and incubated at 28° C. on a shaking machine rotating at 280 revolutions/min for 5 days. A 40 l fermenter which contains 20 l of the nutrient solution described above, plus 0.05% silicone, is inoculated with the preculture thus obtained, and is incubated at 28° C. and 200 revolutions/min (blade stirrer), 10 l air/min, 1.0 bar superimposed pressure for 2 days. The 600 l production fermenter which contains 400 l of the abovementioned nutrient solution, plus 0.03% silicone, is inoculated with this prefermenter. The production culture is incubated at 28° C. for 65 h, a superimposed pressure of 1.0 bar, stirring at 60 revolutions/min (blade stirrer) and aeration with 160 l air/min.

EXAMPLE 2

The culture broth from a 400 l fermentation obtained according to Example 1 is separated in a Westfalia separator at 200–250 l/h. The supernatant is passed through a column of diameter 30 cm packed with 50 l of Lewatit OC 1031 (Bayer). It is washed successively with 500 l of demineralized water and 300 l of 30% strength aqueous methanol, and desorption is carried out with 300 l of methanol. The desorbate is concentrated to dryness under reduced pressure, and 137 g of the *crude* compound according to the invention were obtained (active compound content 1.5%).

EXAMPLE 3

Preparation of the pure compound according to the invention by gel filtration and silica gel chromatography.

50 g of the crude product obtained according to Example 2 were suspended in 2 l of water, and the pH was adjusted to 5.0 with concentrated acetic acid. This suspension is extracted in a separating funnel twice with 2 l each time of a mixture of ethyl acetate/ethanol in the ratio by volume 9:1. The combined organic phases are concentrated to dryness under reduced pressure dissolved in 100 ml of methanol and subjected to gel filtration on Sephadex LH 20 ® in methanol. A column of diameter 7.5 cm and of length 1.25 m is used. The flow rate is 720 ml/h. 200 ml fractions are collected. The fractions active against *Staphylococcus aureus* 1756 in an antibiotic sensitivity test are combined, concentrated under reduced pressures, suspended in water and freeze-dried. Yield: 2.94 g of a 26% pure product.

600 mg of the material thus obtained are dissolved in 100 ml of chloroform with the addition of 60 μl of concentrated acetic acid. A Lobar ® column prepacked with LiChroprep 60 (40–63 μm, Merck, type B) is equilibrated with chloroform, with the addition of 0.1% concentrated acetic acid (v/v), and the solution is applied. After elution with 400 ml of the abovementioned mobile phase, the substance is eluted with a mixture of chloroform/methanol/acetic acid 98/2/0.1. The flow rate is 400 ml/h. 10 ml fractions are collected.

They are analyzed by thin-layer chromatography on silica gel plates (Mercy 5729). The homogeneous fractions which are biologically active and stainable with $FeCl_3/H_2SO_4$ are concentrated to dryness, and the residue is suspended in a little water and freeze-dried. Yield: 76.2 mg of a 98% pure material.

EXAMPLE A

Ruminal fluid was obtained through a ruminal fistula from a wether which received 650 g of coarsely ground compound feed for sheep and 250 g of dry green cobs per day. The compound feed was administered via an automatic feeder in 12 equal portions at intervals of two hours, and the cobs were administered in 2 equal portions at 8.30 and 16.15 h. The ruminal fluid was subjected to the following procedure immediately after it was obtained: 2.5 ml of the ruminal inoculum was initially introduced into a 13 ml test tube through which carbon dioxide was passed and which contained, in addition, the following additives:

100 mg of finely ground compound feed, 7.5 ml of buffer solution, 0.5 ml of a solution containing, or not containing, the compound according to the invention.

The composition of the buffer solution, which was saturated with carbon dioxide before the start of the experiment, was as follows:

| | |
|---|---|
| $Na_2HPO_4$ | 4.61 g per liter of water |
| $NaHCO_3$ | 12.25 g per liter of water |
| NaCl | 0.59 g per liter of water |
| KCl | 0.71 g per liter of water |
| $MgCl_2$ | 0.32 g per liter of water |
| $CaCl_2$ | 0.13 g per liter of water |

The amount of the compound according to the invention necessary to obtain 10, 20, 30 or 40 μg per mixture was dissolved in 0.2 ml of ethanol, and then 4.75 ml of water were added. 0.5 ml of this solution were pipetted into a test tube. The total volume of the fermentation mixture was 10.5 ml after this. The negative controls (that is to say mixtures containing no test substance) Likewise received 0.5 ml of a 5% strength ethanol solution. 4 replicates per dose were carried out. Each test tube was closed with a Bunsen stopper and incubated at 39° C. The mixtures were shaken by hand after 2, 4, 6 and 8 hours. After incubation for 24 hours, 1.0 ml of the fermentation fluid was removed from the mixtures and pipetted into an Eppendorf vessel which contained 0.2 ml of 10% strength phosphoric acid (containing 5.7 μmol of 2-methylvaleric acid). The samples were centrifuged at 10,000 g and the volatile fatty acid concentrations from the supernatant were determined by gas chromatography.

The analytical results were compiled in Table a below. The data (the acetic acid/propionic acid ratio and the total fatty acid production) are shown as a percentage of the negative control:

TABLE a

| Treatment (μg/mixture) | Acetic acid/ propionic acid ratio (%) | Total fatty acids (%) |
|---|---|---|
| 10 | 99.7 | 103.3 |
| 20 | 75.5 | 107.9 |
| 30 | 78.8 | 96.7 |
| 40 | 75.9 | 96.0 |

Table a shows that the ratio of acetate to propionate is essentially reduced and thus improved; owing to the increased formation of propionate from the carbohydrates there is an improvement in the utilization of feed. The increased efficiency of fermentation is only to a slight extent at the expense of the total fatty acid products, as is likewise evident from Table a.

EXAMPLE B:

Broiler chickens:

The livestock, which are housed in cages, are used at an age of 3–5 days for the experiment which extends over a total period of 14 days.

During this time, the livestock receive feed to which the compound according to the invention has been admixed in a dose of 10 or 25 ppm. A negative control (unsupplemented feed) is kept in parallel. At the start of the experiment, all the livestock in an experimental group have the same initial weight.

The criteria used for the assessment are the rates of weight gain, the consumption of feed and the utilization of the feed.

The results are presented in Table b below.
Livestock characteristics and feed
 Graded male boiler hybrids
 24/experiment (4×6)
 Weight 50–65 g
 Feed: Höveler KA 57 complete feed for chickens, with no added antibiotics and coccidiostatics, of the following composition:
Value-determining constituents:
 18% of crude protein
 7% of crude fiber
 8% of ash
 1% of calcium
 0.7% of phosphorus
Composition:
 54% of coarse feed cereal meal (40% corn, 12% wheat)
 17.5% of coarse soy bean meal
 5.2% of corn gluten feed
 5.2% of wheat middlings
 3.1% of fish meal
 3.1% of cassava meal
 3.1% of lucerne meal
 2.1% of wheatgerm (comminuted)
 1.7% of bonemeal
 1.6% of whey powder
 1.4% of limestone
 1.0% of calcium phosphate
 1.0% of molasses.

TABLE b

| Treatment ppm | Weight gain | Consumption of feed | Utilization of feed |
|---|---|---|---|
| 10 | 108% | 97% | 90% |
| 25 | 108% | 93% | 86% |

The novel antibiotic on further purification might possibly comprise a mixture of two or more active compounds and it is intended to embrace each individual active compound and mixtures thereof.

It is understood that the specification and examples are illustrative but not limitative of the present invention and that other embodiments within the spirit and scope of the invention will suggest themselves to those skilled in the art.

We claim:

1. An antibiotic exhibiting an
   a. IR KBr absorption spectrum of the sodium-containing antibiotic at the following wavelengths (expressed in cm$^{-1}$) with characteristic absorption bands

| | |
   |---|---|
   | 3456 | 1265 |
   | 2960 | 1178 |
   | 2910 | 1145 |
   | 1750 | 1115 |
   | 1700 | 1030 |
   | 1635 | 950 |
   | 1540 | 930 |
   | 1395 | 825 | according to FIG. 1, abscissa: wave number in cm$^{-1}$; ordinate: adsorption;
   b. $^1$H nuclear magnetic resonance spectrum according to FIG. 2, reported in parts per million and vibrations per second;
   c. 13C nuclear magnetic resonance spectrum according to FIG. 3;
   d. Elemental analysis (after drying under high vacuum at 30° C. for 2 days): C 61.1–62.3%; H 5.2–6.4%; O 27.5–30.0%;
   e. Empirical formula: $(C_{14-16}, H_{16-20}, O_{4-6})_n$;
   f. Empirical formula of the sodium-containing compound $(C_{29-31}, H_{33-37}, O_{9-11}, Na)$;
   g. Solubility: readily soluble in ethyl acetate, chloroform, MeOH and lower alcohols; sparingly soluble in water and
   h. Stainability: stainable with $FeCl_3H_2SO_4$ after chromatography on thin-layer silica gel plates.

2. A process for the preparation of the antibiotic according to claim 1, comprising cultivating Streptomyces strain BA 9, DSM No. 3025 under aerobic conditions in a nutrient medium which contains sources of assimilable carbon and nitrogen together with mineral salts, until substantial antibacterial activity is imparted to said medium, and then isolating the desired compound from the culture medium.

3. An animal feed premix and/or feed additive comprising an antibacterially or a growth accelerating effective amount of an antibiotic according to claim 1 and an adible diluent.

4. An antibiotic composition comprising an antibacterially effective amount of a compound according to claim 1 and a pharmaceutically acceptable diluent.

5. A unit dose of a composition according to claim 4 in the form of a tablet, capsule or ampule.

6. A method of accelerating the growth of an animal which comprises administering to said animal a growth-accelerating effective amount of a compound according to claim 1.

7. A method of combating bacterial infection which comprises administering to a host which it is desired to be free of bacteria an antibacterially effective amount of a compound according to claim 1.

* * * * *